US006369282B1

(12) United States Patent
Kindler et al.

(10) Patent No.: US 6,369,282 B1
(45) Date of Patent: Apr. 9, 2002

(54) PREPARATION OF ALKYNEDIOLS

(75) Inventors: Alois Kindler, Waldsee; Thomas Preiss, Weisenheim am Sand; Jochem Henkelmann, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/577,127

(22) Filed: May 24, 2000

(30) Foreign Application Priority Data

May 26, 1999 (DE) ......................................... 199 24 020

(51) Int. Cl.$^7$ ............................................... C07C 31/18
(52) U.S. Cl. ......................................................... 568/855
(58) Field of Search .......................................... 568/855

(56) References Cited

FOREIGN PATENT DOCUMENTS

EP            285 755        10/1988

OTHER PUBLICATIONS

Tedeschi et al., 1963, vol. 28, pp. 1740–1743.*
Babler et al., 1996, vol. 61, pp. 416–417.*
Shachat et al., 1962, vo. 27, pp. 198–1504.*
J. Appl. Chem. 1953, 39–42.
J. Org. Chem. 1963, 28, 2480–2483.
J. Org. Chem. 1996, 61, 416–417.
W. Reppe, Liebigs Anm.Chem. 1955, 596, 1–3, 6–11, 25–38.
Russ.J.Org.Chem.,vol.31,No. 9, 1955, pp. 1233–1252.
J.Org.Chem. 1963, 28, 1740–1743.

* cited by examiner

Primary Examiner—Samuel Baris
Assistant Examiner—Elvis O. Price
(74) Attorney, Agent, or Firm—Keil & Weinkauf

(57) ABSTRACT

The process for preparing alkynediols of the formula (I)

$$R^1R^2C(OH)-C\equiv C-C(OH)R^1R^2 \qquad (I)$$

where $R^1$, $R^2$ are each independently H, or a $C_{1-20}$-hydrocarbon radical which may be substituted by one or more $C_{1-6}$-alkyls and/or be interrupted by nonadjacent heteroatoms and/or contain C—C double or triple bonds, by reacting compounds of the formula (II)

$$R^1-C(=O)-R^2 \qquad (II)$$

with acetylene in a polar aprotic solvent is carried out in the presence of basic alkali metal salts as catalysts.

11 Claims, No Drawings

PREPARATION OF ALKYNEDIOLS

The present invention relates to a process for preparing alkynediols by reacting acetylene with carbonyl compounds in the presence of basic catalysts.

Alkynediols are valuable intermediates for preparing, for example, low-foam surfactants, pyrethroids, electrolysis auxiliaries or peroxides.

Various methods of preparing alkynols are known. They can be roughly divided into reactions catalyzed by transition metals and base-catalyzed reactions.

W. Reppe, Liebigs Anm. Chem. 1955, 596, pages 1 to 3, describes, for example, the carbonylation of acetylene with carbonyl compounds in the presence of acetylides of heavy metals of the first transition group of the Periodic Table of the Elements in THF.

On pages 6 to 11 and 25 to 38 it is stated that the ethynylation of ketones can be carried out in aqueous media using alkali metal hydroxides, alkaline earth metal hydroxides, alkali metal carbonates or tertiary amines as catalysts. In addition, copper acetylide can be used as catalyst. In the examples, the preparation of methylbutynol from acetone and acetylene in water using potassium hydroxide as catalyst is mentioned.

R. J. Tedeschi et al., J. Org. Chem. 1963, 28, pages 1715 to 1743, describe the base-catalyzed reaction of acetylene and phenylacetylenes with carbonyl compounds in liquid ammonia under superatmospheric pressure. Here, the reaction to give the corresponding secondary and tertiary acetylenic carbinols is carried out using catalytic amounts of sodium hydroxide or potassium hydroxide.

B. A. Trofimov, Russian Journal of Organic Chemistry, Vol. 31, No 9, 1995, pages 1233 to 1252, describes various reactions using acetylene. Mention is made, inter alia, of ethynylations using the superbasic system KOH/DMSO.

J. H. Babler et al., J. Org. Chem. 1996, 61, pages 416 to 417, describe the alkoxide-catalyzed addition of terminal alkynes onto ketones. Here, the reaction is carried out using tert-butoxide as catalyst. The preparation of alkynediols is not mentioned.

Alkynediols have hitherto been prepared only with use of at least stoichiometric amounts of base. For this purpose, use is frequently made of nucleophilic potassium bases in aprotic solvents, cf. J. Org. Chem. 1963, 28, pages 2480 to 2483 and J. Appl. Chem. 1953, pages 39 to 42, and also EP-A-0 285 755.

It is an object of the present invention to provide a process for preparing alkynediols which avoids the disadvantages of the existing processes and requires the presence of only catalytic amounts of bases.

We have found that this object is achieved by a process for preparing alkynediols of the formula (I)

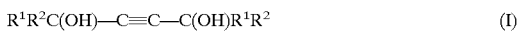

where $R^1$, $R^2$ are each independently H, or a $C_{1-20}$-hydrocarbon radical which may be substituted by one or more $C_{1-6}$-alkyls and/or be interrupted by nonadjacent heteroatoms and/or contain C—C double or triple bonds, by reacting compounds of the formula (II)

with acetylene in a polar aprotic solvent in the presence of basic alkali metal salts, preferably alkali metal alkoxides, as basic catalysts.

It has been found that alkynediols can be obtained in high yield when using alkali metal alkoxides in polar aprotic solvents.

The alkali metal alkoxides can be lithium, sodium, potassium, rubidium or cesium alkoxides. Preference is given to using potassium alkoxides as basic catalysts.

The alcohols on which the alkali metal alkoxides are based are particularly preferably selected from among alkynols of the formula (III)

where $R^1$ and $R^2$ are as defined above, and straight-chain or branched $C_{1-12}$-alkanols.

The basic catalyst can also be prepared in situ from alkali metal hydrides, acetylene and the compound of the formula (II).

In the reaction, certain amounts of alkynols of the formula (III) are also formed in addition to alkynediols. For this reason, the use of these compounds or preparation of them in situ is advantageous. Otherwise, particular preference is given to using a potassium $C_{1-6}$-alkanolate, for example one selected from among potassium methoxide, potassium ethoxide, potassium propoxides, potassium butoxides, potassium pentoxides or potassium hexoxides. The alkanolates can be straight-chain or branched.

The basic catalyst is preferably used in an amount of from 5 to 65 mol %, particularly preferably from 10 to 30 mol %, based on acetylene.

The reaction is preferably carried out at from −20 to +60° C., particularly preferably from −10 to +40° C., in particular from 10 to 30° C., and at a pressure of from 0.1 to 10 bar, particularly preferably from 0.5 to 5 bar, in particular atmospheric pressure.

The polar aprotic solvent is preferably selected from among tetrahydrofuran (THF), N-methylpyrrolidone (NMP), dimethyl sulfoxide (DMSO) and mixtures thereof, with up to 20% by weight of the solvent being able to be replaced by nonpolar hydrocarbons. The solvent is particularly preferably based on THF. In particular, the proportion of nonpolar hydrocarbons is less than 10% by weight, especially less than 5% by weight. In particular, only THF is used as solvent.

In the reaction of the present invention, it is possible to use a wide variety of carbonyl compounds of the formula (II). Preferably $R^1$ and $R^2$ are each independently H or a $C_{1-2}$-hydrocarbon radical which may be straight-chain or branched. Particularly preferably, $R^1$ and $R^2$ are independently H or $C_{1-6}$-alkyl. Examples of suitable carbonyl compounds are formaldehyde and acetone.

In the process of the present invention, the basic catalyst is preferably initially charged in the polar aprotic solvent, whereupon acetylene and the carbonyl compounds are metered in and reacted in parallel. The mixture can then be worked up hydrolytically.

The invention is illustrated by the examples below.

EXAMPLES

Example 1

Preparation of butynediol 400 g of THF and 4 g of potassium hydride plus 5.6 g of propynol were introduced at 30° C. into a double-wall reactor provided with a stirrer and the mixture was stirred at this temperature for 15 minutes. The solution was cooled to 10° C. and held at this temperature during the reaction. 60 g of paraformaldehyde (2 mol) and 26 g of acetylene (1 mol) were introduced in parallel over a period of 1 hour. After an after-reaction time of 15 minutes, the mixture was hydrolyzed with 150 g of water. After phase separation, the aqueous phase was acidified with $H_3PO_4$, extracted three times with diethyl ether, and the extracts were combined with the organic phase and analyzed. 3.83% by weight, based on formaldehyde, of residue were found. The conversion of formaldehyde was 96%. A yield of 76% of propynol and 20% of butynediol was found.

Example 2

Preparation of dimethylhexynediol 400 g of THF and 12 g of potassium hydride (0.3 mol) plus 34 g of isobutanol (0.3 mol) were introduced at 30° C. into a double-wall reactor provided with a stirrer and the mixture was stirred at this temperature for 15 minutes. The solution was maintained at 30° C. during the reaction. 58 g of acetone (1 mol) and 26 g of acetylene (1 mol) were introduced in parallel over a period of 2 hours. After an after-reaction time of 15 minutes, the mixture was hydrolyzed with 150 g of water. After phase separation, the aqueous phase was acidified with $H_3PO_4$, extracted three times with diethyl ether, and the extracts were combined with the organic phase and analyzed. The conversion of acetone was 96%. A yield of 74% of methylbutynol and 22% of dimethylhexynediol was found.

Example 3

Preparation of dimethylhexynediol 400 g of THF and 120 g of potassium isobutoxide in xylene (0.6 mol) were introduced into a double-wall reactor provided with a stirrer. The suspension was brought to 30° C. and maintained at this temperature during the reaction. 116 g of acetone (2 mol) and 26 g of acetylene (1 mol) were introduced in parallel over a period of 2 hours. After an after-reaction time of 15 minutes, the mixture was hydrolyzed with 150 g of water. After phase separation, the aqueous phase was discarded. The organic phase was analyzed. The conversion of acetone was 75%. A yield of 19% of methylbutynol and 56% of dimethylhexynediol was found.

Example 4

Preparation of dimethylhexynediol 400 g of THF and 24 g of potassium hydride (0.6 mol) were introduced into a double-wall reactor provided with a stirrer. The suspension was brought to 30° C. and maintained at this temperature during the reaction. 116 g of acetone (2 mol) and 26 g of acetylene (1 mol) were introduced in parallel over a period of 2 hours. After an after-reaction time of 15 minutes, the mixture was hydrolyzed with 150 g of water. After phase separation, the aqueous phase was discarded. The organic phase was analyzed. The conversion of acetone was 97%. A yield of 7% of methylbutynol and 91% of dimethylhexynediol was found.

The reactions were each carried out at a pressure of 1013 mbar.

We claim:

1. A process for preparing alkynediols of the formula (I)

$$R^1R^2C(OH)-C\equiv C-C(OH)R^1R^2 \qquad (I)$$

where $R^1$, $R^2$ are each independently H, or a $C_{1-20}$-hydrocarbon radical which may be substituted by one or more $C_{1-6}$-alkyls and/or be interrupted by nonadjacent heteroatoms and/or contain C—C double or triple bonds, by reacting compounds of formula (II)

$$R^1-C(\equiv O)-R^2 \qquad (II)$$

with acetylene in a polar aprotic solvent in the presence of basic alkali metal salts as catalysts, wherein alkali metal alkoxides are used as basic catalysts, and wherein the alcohols on which the alkali metal alkoxides are based are selected from among alkynols of the formula (III)

$$R^1R^2C(OH)-C\equiv CH \qquad (III).$$

2. The process of claim 1, wherein potassium alkoxides are used as basic catalysts.

3. The process of claim 1, wherein the basic catalyst is prepared in situ from alkali metal hydrides, acetylene and the compound of the formula (II).

4. The process of claim 1, wherein the basic catalyst is used in an amount of from 5 to 65 mol %, based on acetylene.

5. The process of claim 1, wherein the reaction is carried out at from −20 to 60° C. and at a pressure in the range from 0.1 to 10 bar.

6. The process of claim 1, wherein the polar aprotic solvent is selected from among THF, NMP, DMSO and mixtures thereof, with up to 20% by weight of the solvent being able to be replaced by nonpolar hydrocarbons.

7. The process of claim 1, wherein $R^1$ and $R^2$ are independently H or $C_{1-6}$-alkyl.

8. The process of claim 3, wherein the basic catalyst is used in an amount of from 5 to 65 mol %, based on acetylene.

9. The process of claim 3, wherein the reaction is carried out at from −20 to 60° C. and at a pressure in the range from 0.1 to 10 bar.

10. The process of claim 3, wherein the polar aprotic solvent is selected from among THF, NMP, DMSO and mixtures thereof, with up to 20% by weight of the solvent being able to be replaced by nonpolar hydrocarbons.

11. The process of claim 3, wherein $R^1$ and $R^2$ are independently H or $C_{1-6}$-alkyl.

* * * * *